United States Patent [19]

Tanaka et al.

[11] Patent Number: 5,641,643
[45] Date of Patent: Jun. 24, 1997

[54] HORSESHOE CRAB AMEBOCYTE LYSATE FACTOR G ACTIVATION INHIBITOR

[75] Inventors: Shigenori Tanaka, Tokyo; Jun Aketagawa, Tachikawa; Makoto Ohki, Kokubunji; Shoji Takahashi; Hiroshi Tamura, both of Higashiyamato; Yuko Shibata, Tokyo, all of Japan

[73] Assignee: Seikagaku Kogyo Co., Ltd., Tokyo, Japan

[21] Appl. No.: 542,699

[22] Filed: Oct. 13, 1995

Related U.S. Application Data

[63] Continuation of Ser. No. 246,920, May 20, 1994, Pat. No. 5,474,984, which is a continuation of Ser. No. 822,740, Jan. 21, 1992, abandoned, which is a division of Ser. No. 474,057, filed as PCT/JP89/00903, Sep. 1, 1989, Pat. No. 5,155,032.

[30] Foreign Application Priority Data

Sep. 1, 1988 [JP] Japan .................. 63-216341

[51] Int. Cl.$^6$ .............. C12Q 1/37; C12Q 1/34; C07H 3/06; C08B 37/18
[52] U.S. Cl. .............. 435/23; 435/18; 435/34; 536/123.1; 536/123.12
[58] Field of Search .............. 514/23, 54; 536/123.1, 536/123.12; 435/23, 18, 34

[56] References Cited

U.S. PATENT DOCUMENTS

| | | |
|---|---|---|
| 4,454,315 | 6/1984 | Sasaki et al. . |
| 4,851,224 | 7/1989 | McAnalley . |
| 4,970,152 | 11/1990 | Ashida et al. . |
| 5,047,353 | 9/1991 | Tsuchiya et al. . |
| 5,155,032 | 10/1992 | Tanaka et al. . |
| 5,179,006 | 1/1993 | Matuura et al. . |
| 5,318,893 | 6/1994 | Matuura et al. ............. 435/23 |

FOREIGN PATENT DOCUMENTS

| | | |
|---|---|---|
| 0330991 | 9/1989 | European Pat. Off. . |
| 0333187 | 9/1989 | European Pat. Off. . |
| 58-13517 | 1/1983 | Japan . |
| 59-28474 | 2/1984 | Japan . |

OTHER PUBLICATIONS

Biochemical & Biophysical Research Communications, vol. 101, No. 2, 1981, pp. 434–439, Gelation of Limulus Amoebocyte Lysate by an Antitumor (1→3)-β-D-Glucan.

Bacterial Endotoxins: Structure, Biomedical Significance, and Detection with Limulus Amebocyte Lysate Test, pp. 53–64; Biomedical Characterization of Limulus Clotting Factors and Inhibitors which interact with Bacterial Endotoxins, 1985, Alan R. Liss, Inc., Morita et al.

(List continued on next page.)

*Primary Examiner*—John Kight
*Assistant Examiner*—Everett White
*Attorney, Agent, or Firm*—Sherman and Shalloway

[57] ABSTRACT

This invention relates to a horseshoe crab amebocyte lysate factor G activation inhibitor comprising as an active ingredient a polyglycoside containing at least one poly-(1→3)-β-D-glucoside structure portion consisting of 2 to 370 (1→3)-β-D-glucoside structural units of the following formula

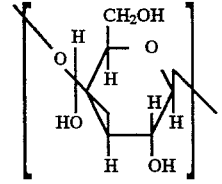

which are continuously bound to one another. This inhibitor is useful for inhibiting the activation of factor G which may exist in horseshoe crab amebocyte lysate used in the Limulus test.

13 Claims, 2 Drawing Sheets

OTHER PUBLICATIONS

Biological Bulletin, vol. 169, 1985, pp./ 661–674; The Effects of 1,3–Glucans on Blood coagulation and Amebocyte Release in the Horseshoe Crab Limulus Polyphemus. Clinica Chemica Acta, vol. 149, No. 1, 1985 (Elsevier Science Publishers B.V.), Obayashi, et al., "A New Chromogenic Endotoxin–Specific Assay using Recombined Limulus Coagulation Enzymes and its Clinical Applications" pp. 55–65.

FEBS Letters, vol. 129, No. 2, 1981 Jul. (North–Holland Biomedical Press), Morita, et al., "A New (1–3)–β–D–Glucan Mediated Coagulation Pathway found in Limulus Amebocytes", pp. 318–321.

Journal of Protein Chemistry, vol. 5, No. 4, 1986, Iwanaga, et al. "The Hemolymph Coagulation System in Invertebrate Animals," pp. 255–268.

HORSESHOE CRAB AMEBOCYTE LYSATE FACTOR G ACTIVATION INHIBITOR

This is a Rule 60 Continuation Application of Ser. No. 08/246,920, filed May 20, 1994, now U.S. Pat. No. 5,474,984, which is a Rule 62 Continuation Application of Ser. No. 07/822,740, filed Jan. 21, 1992, now abandoned, which is a divisional of application Ser. No. 07/474,057, filed as PCT/JP89/00903, Sep. 1, 1989, now U.S. Pat. No. 5,155,032, issued Oct. 13, 1992.

TECHNICAL FIELD

This invention relates to an agent which inhibits activation of a certain enzyme precursor, and more specifically, to a factor G activation inhibitor, or a substance which inhibits activation of a (1→3)-β-D-glucan sensitive factor, factor G, of a system whose coagulation is started by reaction with (1→3)-β-D-glucan among factors involved in the clotting system of horseshoe crab amebocyte lysate.

BACKGROUND TECHNOLOGY

In 1964, Levin and Bang discovered the phenomenon in which horseshoe crab (limulus) amebocyte lysate (hereinafter sometimes abbreviated as LAL) is immediately coagulated (gelled) by a Gram-negative bacterial endotoxin [J. Levin and F. B. Bang: Bull. Johns Hopkins Hospital, 115, 265–274 (1964)]. Since then, LAL has been widely utilized as the so-called Limulus Test reagent in a method of specific detection of endotoxins. Today, three genera, four species of horseshoe crab survive throughout the world and *Limulus polyphemus*, *Tachypleus tridentatus*, *Tachypleus gigas* and *Carcinoscorpius rotundicauda* are known. "Limulus Test" reagents comprising the amebocyte lysate of *L. Polyphemus* occurring in the United States and *T. tridentatus* occurring in Japan and China have been commercialized. [See, for example, Progress in Clinical and Biological Research: volume 93; "Endotoxins and their Detection with the Limulus Amebocyte Lysate Test", edited by Stanly W. Watson, Jack Levin and Thomas J. Novitsky, published in 1982 by Alan R. Liss Inc., pages 7–24, entitled: The Limulus Test and Bacterial Endotoxins: Some Perspectives by J. Levin.]

LAL was first considered to react specifically only with endotoxins. Recent studies have shown that LAL has been found to react with (1→3)-β-D-glucan as well as endotoxin. The coagulation system of LAL, like the mammalian blood coagulation system, consists of two or more cascade reactions of coagulation factors, and include not only an endotoxin-mediated pathway (factor C pathway), but also a pathway to be triggered by (1→3)-β-D-glucan (factor G pathway) [T. Morita et al., FEBS LETTERS, 129, 318–321 (1981), and S. Iwanaga et al., J. Protein Chem., 5, 255–268 (1986)]. Accordingly, work has been done in order to render the Limulus test as endotoxin-specific as possible. For example, T. Obayashi et al., Clin. Chim. Acta, 149, 55–65 (1985) proposed a method of determining an endotoxin by using a reagent obtained by removing factor G from LAL by separation and reconstitution of the coagulation factors. An endotoxin specific assay kit in accordance with this method is sold under the tradename "Endospecy®" by Seikagaku Kogyo Co., Ltd.

The above-proposed assay method has a very strong demand as an edndotoxin-specific assay. However, this method involves certain disadvantages to be described.

(1) To separate and remove factor G from limulus amebocyte lysate composed of a plurality of coagulation factors, it is necessary to perform the operation of separating the individual factors in the absence of an endotoxin or (1→3)-β-D-glucan. Accordingly, the endotoxin or (1→3)-β-D-glucan must be removed completely in advance from tools, devices and chemicals used in the separating operation for fractionation.

(2) As the separating operation proceeds, the amebocyte lysate becomes diluted, and it must occasionally be concentrated.

(3) Every time a separating operation is carried out, the factors decrease in activity or a loss of the fractions occurs.

(4) The coagulogen (clottable protein precursor) is separated and removed together with factor G.

Because of these disadvantages, the above proposed assay method can be applied only to a chromogenic method, and cannot be applied to methods utilizing the gellation phenomenon such as a gellation method, turbidimetry and turbidimetric kinetic assay. In the course of studying a pathway to be triggered by (1→3)-β-D-glucan (factor G pathway) in the LAL coagulation mechanism, the present inventors unexpectedly found that among (1→3)-β-D-glucans heretofore considered to be involved only in the activation of factor G, one containing a structural portion consisting of a specific number of continuously bound (1→3)-β-D-glucoside structural units, quite contrary, shows a factor G inhibiting action. This finding has led to accomplishment of the present invention.

DISCLOSURE OF THE INVENTION

The present invention provides a horseshoe crab amebocyte lysate factor G activation inhibitor comprising as an active ingredient a polyglycoside containing at least one poly-(1→3)-β-D-glucoside structure portion consisting of 2 to 370 (1→3)-β-D-glucoside structural units (molecular weight 162) of the following formula

(I)

which are continuously bound to one another.

The present invention also provides a method of inhibiting the activation of factor G existing in limulus amebocyte lysate (LAL), which comprises adding an effective amount of the polyglycoside to the limulus amebocyte lysate.

The present invention will be explained in more detail.

The polyglycoside used as an active ingredient in the inhibitor of this invention contains per molecule at least one poly-(1→3)-β-D-glucoside structure portion consisting of 2 to 370, preferably 3 to 310, more preferably 4 to 180, (1→3)-β-D-glucoside structural units of the following formula (I)

continuously bound to one another [this poly-(1→3)-β-D-glucoside structure portion is referred to simply as "poly-(1→3)glucoside structure portion"].

So long as the polyglycoside used in this invention contains at least one poly-(1→3)glucoside structure portion per molecule, the structure of the remaining portion of the polyglycoside molecule is not particularly limited, and may be selected widely. It is important however that the other structural portion should not substantially react with endotoxins and the factor C activation system. For example, the polyglycoside used in this invention consists substantially of one poly-(1→3)glucoside structure portion, for example poly-(1→3)-β-D-glucoside represented by the following formula (I-1)

wherein n is an integer of 2 to 370, preferably 3 to 310, more preferably 4 to 180.

Alternatively, it may be of a structure resulting from binding of a carbohydrate chain composed of at least one (1→4)-β-D-glucoside structural unit represented by the following formula

(II)

and/or at least one (1→6)-β-D-glucoside structural unit represented by the following formula (III)

and/or at least one modified β-D-glucoside structure of the formula (IV)

(V)

(VI)

In the above formulae (IV), (V) and (VI), at least one of $R_1$, $R_2$ and $R_3$ represents a chemically introducible functional group, such as a methyl group, a hydroxymethyl group, a carboxymethyl group, an acetyl group, a sulfuric acid group or a phosphoric acid group, or a metal salt, an ammonium salt or an organic amine salt thereof, and the remainder represents a hydrogen atom.

The above carbohydrate chain may be bound as a branched chain to the poly-(1→3)glucoside structure portion).

Furthermore, the polyglycoside used in this invention may be one in which two or more poly-(1→3)glucoside structural portions are linked with other carbohydrate chain structural portions interposed between the poly-(1→3) glucoside structural portions as shown by the following formula $A_1$-$B_1$-$A_2$$B_2$ wherein each of $A_1$, $A_2$ . . . represents a poly-(1→3)-β-D-glucoside structure portion composed of 2 to 370, preferably 3 to 310, more preferably 4 to 180 (1→3)-β-D-glucoside structural units of formula (I) continuously bound to one another, the number of the units of formula (I) in the structural portions $A_1$, $A_2$, . . . may be different, and $B_1$, $B_2$, . . . represent other carbohydrate chain structure portions which are identical or different. The other carbohydrate chain structural portions represented by $B_1$, $B_2$, . . . may be, for example, structural portions composed of one structural unit of formula (II), (III), (IV), (V) or (VI) or two or more such structural units.

Furthermore, the polyglycoside used in this invention may be of such a structure that the above poly-(1→3) glucoside structural portion is composed of long-chain poly-(1→3)-β-D-glucoside structural portions each of which is composed of at least 371 (1→3)-β-D-glucoside structural units of formula (I) continuously bound to one another, with the other carbohydrate chain structures of formula $B_1$, $B_2$ . . . interrupting the chain.

Accordingly, the polyglycoside used in this invention is not particularly limited in molecular weight so long as it contains at least one poly-(1→3)-glucoside structural portion per molecule. Conveniently, however, it generally has a molecular weight of not more than 500,000, preferably 500 to 240,000, more preferably 650 to 80,000. If its molecular weight falls outside the above range, its solubility in water is reduced, and the viscosity of the solution increases to make it difficult to handle, or disadvantages will arise in preparing an endotoxin assay kit of a consistent quality.

Preferably, the polyglycoside used in this invention consists substantially of at least one poly-(1→3)glucoside structural portion per molecule. It may, however, contain another polyglycoside containing a high-molecular-weight poly-(1→3)-β-D-glucoside structural portion composed of at least 371 (1→3)-β-D-glucoside structural units of formula (I) continuously bound to each other. This is because the polyglycoside in accordance with this invention binds to the factor G being an initiation factor or factor G activation pathway of LAL more rapidly and strongly than the high-molecular-weight poly-(1→3)-β-D-glucoside which is a factor G activating substance and thus inhibits activation of factor G and its inhibiting action is not substantially affected by the presence of the high-molecular-weight poly-(1→3)-β-D-glucoside.

When the polyglycoside containing another component is used as an inhibitor, the amount of the polyglycoside in the inhibitor is not particularly limited. However, if its amount is too small, the poly-glycoside must be used in a large amount to inhibit factor G, and this is not economical. Generally, the amount of the polyglycoside in the inhibitor is desirably at least 5% by weight, preferably at least 10% by weight, more preferably at least 20% by weight.

The molecular weight of the polyglycoside of the present invention is determined by performing gel permeation chromatography under the conditions indicated below using a standard substance of a known molecular weight, drawing a standard curve, then performing gel permeation chromatography under the same conditions on a test sample, and comparing the results with the standard curve.

Conditions Used in Gel permeation Chromatography

Column: TSK gel G-PWXL series (Tosoh Co., Ltd.) 7.8×300 mm, several columns of several types Mobile phase: 0.3M NaOH Flow rate: 0.5 ml/min.

Sample concentration: 0.1–5 mg/ml

Sample volume injected: 0.1 ml

Column temperature: room temperature

Method of detection: Measurement by a differential refractometer (made by LKB Company), or carbohydrate assay by the phenol-sulfuric acid method.

Standard substance: TSK standard polyethylene oxide (a product of Tosoh Co., Ltd.) and polyethylene glycol (a product of Nakarai Chemicals Co., Ltd.), 10 types having a weight average molecular weight ranging from 1,000 to 860,000.

The polyglycoside having the above-described properties used as a factor G activation inhibitor in this invention may be one derived from nature, or a synthetic product, or a partially chemically modified product of a poly-(1→3)-β-D-glucoside containing at least three (1→3)-β-D-glucoside structural units of formula (I). Usually, polyglycosides derived from nature are easy to obtain. Specific examples of the polyglycoside are given below.

(1) Substantially straight-chain polyglycosides composed substantially of the (1→3)-β-D-glucoside structural units of formula (I) alone, for example (1→3)-β-D-glucans derived from bacteria of the genus *Alcaligenes*; paramylon derived from flagellates (Euglena); β-glucans from the fibrous tissues of higher plants or callose extracted from the sieve tube; D-glucose polymer composed of (1→3)-β-bonds of higher degrees of polymerization contained in partial hydrolyzates of laminarans derived from brown algae of the genus *Laminaria* or *Eisenia*, or (1→3)-β-D-glucans; laminaridextrins having degrees of polymerization of 10 to 20; and laminarioligosaccharides having degrees of polymerization of less than 10.

(2) Polyglycosides containing both the poly-(1→3)-β-D-glucoside structural units of formula (I) and the (1→6)-β-D-glucoside structural units of formula (III). Examples are given below.

(a) Polyglycosides in which glucose or a glucose polymer resulting from linking of one to several (1→6)-β-bonds with a main chain composed of (1→3)-β-bonds is incorporated, such as laminarans derived from brown algae of the genus *Eisenia*.

(b) Polyglycosides resulting from attaching a carbohydrate chain of (1→3)-β-bonds through (1→6)-β-bond to the glucose or glucose polymer linked by (1→3)-β-bonds in (a), which may further include another carbohydrate portion in a part of the carbohydrate chain, for example laminatans derived from brown algae of the genus *Laminaria*, chrysolaminarans derived from diatoms such as *Ochromonas, Phaeodactylum, Skeletonema, Biddulphia, Coscinodiescus* and *Chaetoceros* and pachyman derived from *Poria*.

(c) Polyglycosides having more branches and being dendriform, such as a glucan derived from the cell wall of *Phytophthora*.

(d) polyglycosides in which glucose is linked through (1→6)-β-bonds with straight-chain glucan composed of (1→3)-β-bonds, such as sclerotan derived from *Sclerotinia* having a single glucosyl branch on every 3 glucosyl residues of the main chain, schizophyllan from *Schizophyllum*, scleroglucans derived from *Sclerotium, Corticium* and *Stromatinia*, and polyglycosides in which glucose is bound to a straight-chain glucan composed of (1→3)-β-bonds via (1→6)-β-bonds at a rate of two glucosyl residues per 5 glucose units of the straight-chain glucan, such as lentinan of *Lentinus*.

(e) A straight-chain glucan composed of (1→6)-β-bonds having a plurality of (1→3)-β-glucose chains branched from the C-3 portion of glucose residue of the main chain, such as β-glucan derived from the cell wall of *Saccharomyces* (bakers' yeast).

(3) Polyglycosides containing both the (1→3)-β-D-glucoside structural units of formula (I) and the (1→4)-β-glucoside structural units of formula (II), for example lichenans derived from *Cetraria, Usnea* and *Evernia*, and β-glucan contained in barley albumin, which are composed of the polyglycoside consisting of portions of (1→4)-β-oligoglucoside is linked through (1→3)-β-bonds containing (1→3)-β-oligoglycosides at intervals.

Some of the polyglycosides described above are commercially available, and may be utilized directly as the inhibitor of this invention. As required, the carbohydrate chain is partially decomposed and/or subjected to a separation treatment, and a fraction rich in a polyglycoside comprising the aforesaid specific amount of the (1→3)β-D-glucoside structural units of formula (I) is prepared. This fraction may be utilized as the inhibitor of the invention.

The partial decomposition and the separation treatment of the carbohydrate chain may be carried out by known methods. The partial decomposition of the carbohydrate chain may be carried out, for example, by hydrolysis with acids or alkalies or β-glucanase, acetolysis, or sonication. The fractionation based on molecular weight may be carried out by using a fractional precipitation method with organic solvents such as alcohols, acetone or ethers or salts or by fractionation with a molecular sieve agent or a molecular sieve membrane.

Part of the carbohydrate chains of the polyglucosides exemplified in (1) to (3) above may be chemically modified with an alkyl group such as a methyl group, a hydroxyalkyl group such as a hydroxymethyl group, a carboxyalkyl group such as a carboxymethyl group, an acid group such as an acetyl group, a sulfuric acid group, a phosphoric acid group or another functional group. Such a functional group may be introduced by methods known per se [see, for example, (1) "Seikagaku Kenkyuhou I" (Methods of Studying Biochemistry I") 283–303 (1967) edited by Ando, Terayama, Nishizawa and Yamakawa, Asakura Shoten, and (2) Whistler, R. L. ed.: Methods in Carbohydrate Chemistry III, 193–267, 271–331 (1964), Academic Press, New York and London]. By partial chemical modification of a (1→3)-β-D-glucan with a molecular weight of at least about 60,000 having a factor G activating action, the number of (1→3)-β-D-glucoside structural units of formula (I) continuously bound to each other in the poly-(1→3)-β-D-glucoside structure portion is adjusted to 370 or less. This chemically modified glucan may be used as the inhibitor of this invention.

Specific examples of the polyglycoside preferably used in this invention are shown below.

Laminarioligosaccharide having a molecular weight of 342 to 1,638;

laminaridextrin having a molecular weight of 1,800 to 3,258;

(1→3)-β-D-glucan having an average molecular weight of 2,000 to 60,000;

laminaran having an average molecular weight of 3,000 to 23,000;

sclerotan having an average molecular weight of 3,000 to 20,000, schizophyllan having an average molecular weight of not more than 500,000;

lentinan having an average molecular weight of not more than 1,100,000;

a water-soluble function of baker's yeast glucan having an average molecular weight of not more than 12,000;

lichenan having an average molecular weight of not more than 33,000;

barley β-glucan having an average molecular weight of not more than 200,000;

partially carboxymethylated (1→3)-β-D-glucan having an average molecular weight of 40,000 to 240,000 obtained, for example, by partial carboxymethylation of Curdlan, and its metal salts (the degree of substitution: 0.003 to 1.0).

Partially carboxymethylated laminaran having an average molecular weight of not more than 23,000 and its salts (the degree of substitution: not more than 1.0);

partially methylated (1→3)-β-D-glucan having an average molecular weight of not more than 80,000 (the degree of substitution: 0.003 to 1.0); and partially sulfated laminaran having an average molecular weight of not more than 23,000 and its salt (the degree of substitution: not more than 1.0).

As will be demonstrated by working examples given later on, the polyglycosides in accordance with this invention have the action of strongly inhibiting the activation of factor G in LAL, and therefore can be used to specifically detect and assay endotoxins in an assay sample by the Limulus test without adverse effects by the factor G system. The polyglycoside as a factor G activation inhibitor may be used in the Limulus test in an amount larger than that required to inhibit the activation of factor G in LAL completely. The polyglycoside may be added either (1) at the time of detection and assay, (2) to LAL beforehand, or (3) at the time of extracting and preparing LAL.

The amount of the inhibitor required to completely inhibit activation of factor G in LAL can be determined by, for example, the following procedure. Under ice cooling, a fixed amount of a factor G activating substance (containing no endotoxin or containing a minimum of a factor G activation inhibitor) sufficient to activate LAL under ordinary assay conditions is added to a fixed amount of LAL. To the mixture is added an inhibitor (free from an endotoxin) in varying concentrations. The reaction is carried out under the same conditions as in the case of using ordinary LAL. Under these conditions, the concentration of the inhibitor which inhibits the activation of LAL completely is determined.

The inhibitor having the above-determined concentration is added to a fixed amount of LAL, and the factor G activating substance is further added in varying amounts, and it is confirmed that in any concentration of the factor G activating substance, LAL is not activated.

By the above operation, the amount (concentration) of the inhibitor required to completely inhibit the activation of factor G in a fixed amount of LAL can be determined.

The amount of the factor G activation inhibitor required to completely inhibit the activation of factor G in commercial lysates is shown in Table 1.

Table 1

| Lysate (tradename) | GI * (ng/ml LAL) |
| --- | --- |
| Pregel (Seikagaku Kogyo Co., Ltd.) | 120 |
| Pregel-S (same as above) | 120 |
| Limulus-Test wako (Wako Pure Chemical Industries, Ltd.) | 100 |
| Limulus HS-Test wako (same as above) | 100 |
| Pyrotell (Cape Cod, Inc.) | 120 |
| Pyrosate (Haemachem Inc.) | 230 |
| Pyrotest (Difco Laboratories Inc.) | 230 |
| Pyrogent (Whittaker Bioproducts, Inc.) | 50 |
| Pyrodick (Seikagaku Kogyo Co., Ltd.) | 230 |
| Toxicolor (same as above) | 450 |

Table 1-continued

| Lysate (tradename) | GI * (ng/ml LAL) |
| --- | --- |
| QCL-1000 (Whittaker Bioproducts, Inc.) | 50 |
| Coatest Endotoxin (Kabi Vitrum) | 230 |

(Note)
* factor G activation inhibitor: GPC fraction 4 of the formic acid-degraded product of Curdlan obtained in Preparation Example 4-1 (sample No. 14 in Table 2).

As is clear from the required amounts of the inhibitors, the suitable amount of the polyglycoside in accordance with this invention to be contained in the Limulus test reagent composed of LAL is at least 50 ng, preferably at least 100 ng, more preferably 100 to 230 ng, especially preferably 230 to 500 ng, per ml of LAL, The method of producing the factor G activation inhibitors of this invention, their functional mechanism, Limulus test reagent kits comprising the inhibitors will be described in detail.

Method of Preparing Factor G Activation Inhibitor of the Invention

The factor G activation inhibitor of this invention can be prepared, for example, by the methods shown in the following Preparation Examples. Commercial (1→3)-β-D-glucans which are within the scope of this invention may be directly used.

PREPARATION EXAMPLE 1

Preparation from commercial Curdlan by molecular sieve chromatographic fractionation:

One gram of sample No. 101 Curdlan (a reagent produced by Wako Pure Chemical Industries, Lot No. PEQ 9080, Mn>136,000, Mw/Mn>2.76) was dissolved in 0.3M NaOH at a concentration of 5 mg/ml. Each 100 microliter aliquot of the solution was subjected to gel permeation chromatography (GPC hereinafter) under the following conditions.

Columns: TSK gel G6000 $PW_{XL}$ and G5000 $PW_{XL}$ (both 7.8×300 mm) connected in series Mobile phase: 0.3M NaOH Flow rate: 0.5 ml/min.

Figure 1:
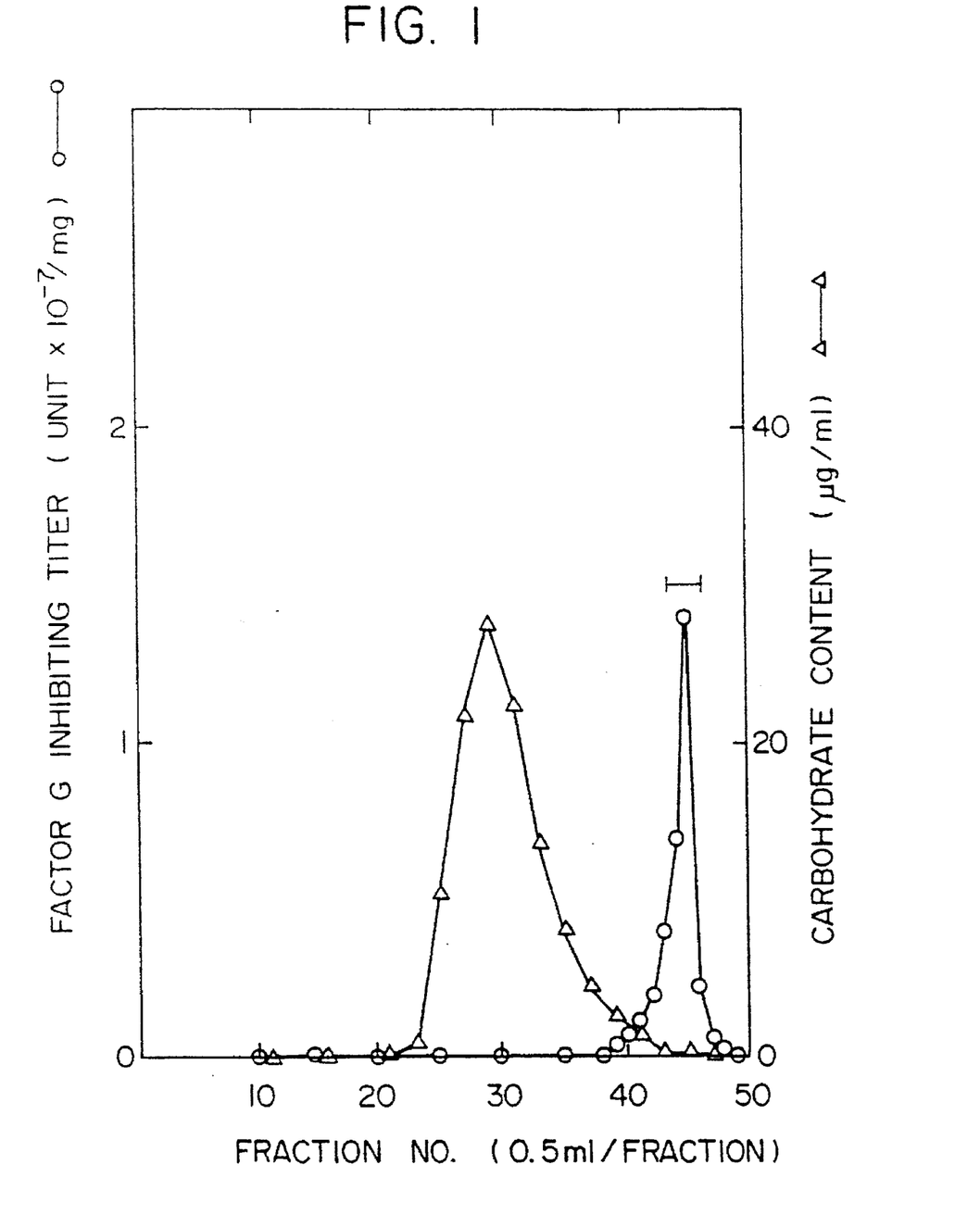
FIG. 1 shows a molecular sieve GPC fractionation pattern of commercial Curdlan.
Figure 2:
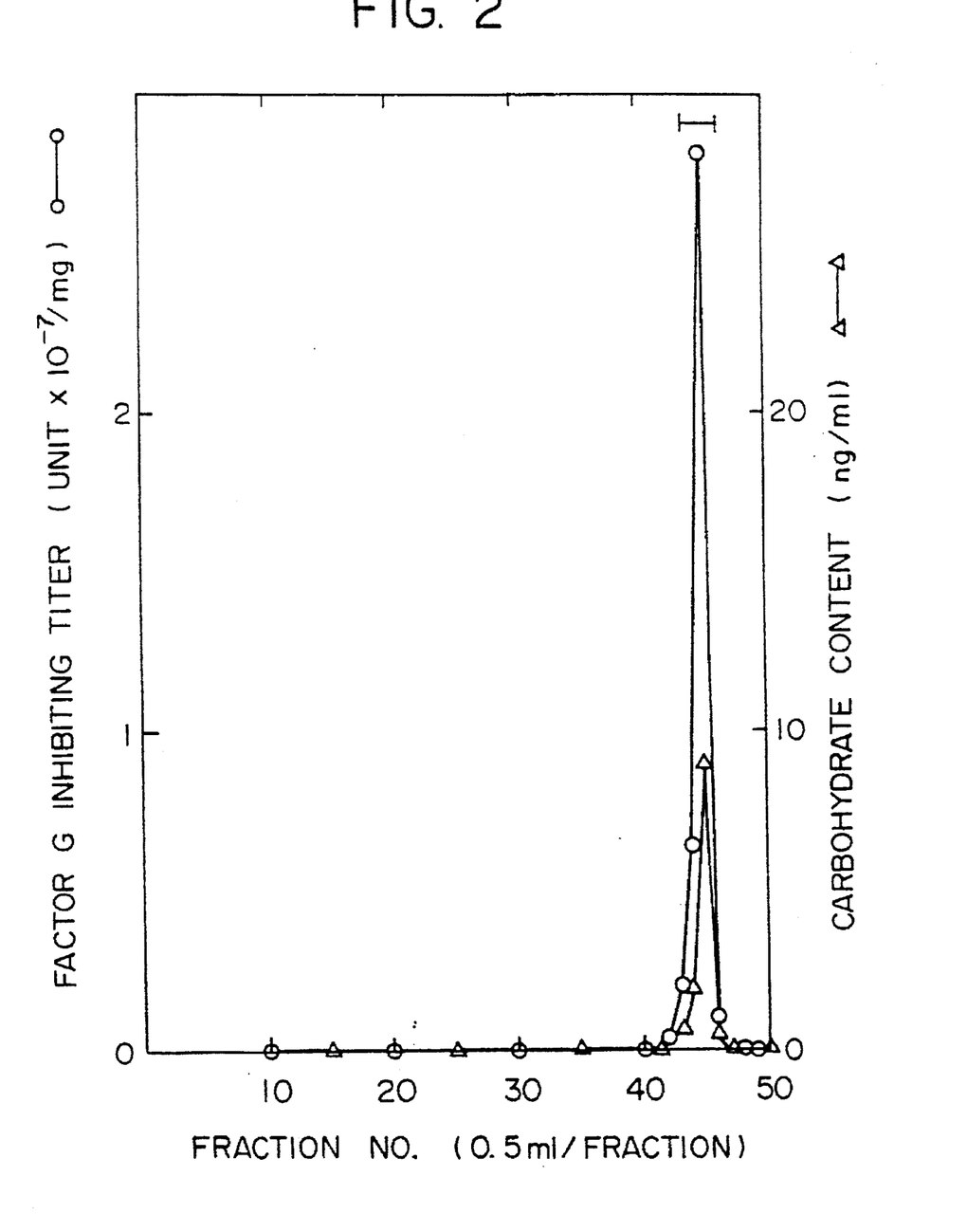
FIG. 2 shows re-chromatographic fractionation patterns of fractions Nos. 44 to 46 in FIG. 1.

Low molecular weight fractions (Nos. 44 to 46) eluted were collected and again subjected to chromatography to give 0.015 mg of a sample (sample No. 1) having a number average molecular weight of 3,050 and a polydispersity of 1.29. The GPC fractionation pattern is shown in FIG. 1. The fractionation patterns of fractions Nos. 44 to 46 in FIG. 1 which were again chromatographed are shown in FIG. 2.

Sample No. 1 was digested with β-1,3-glucanase (Zymolyase 100T, a product of Seikagaku Kogyo Co., Ltd.). The enzyme digestion product was analyzed by GPC under the following conditions.

Columns: TSK gel G4000 $PW_{XL}$, G3000 $PW_{XL}$ and G2500 $PW_{XL}$ connected in series Mobile phase: Distilled water Flow rate: 0.6 ml/min.

The carbohydrate composition of the enzyme-digestion product was determined to be: glucose 40%, laminaribiose 30%, laminaritriose 20%, laminaritetraose laminaripentaose 2% (recovery ratio 94%). The analysis showed that the carbohydrate structure of sample No. 1 is β-polyglucoside having a (1→3)-β-D-glucoside structure portion.

PREPARATION EXAMPLE 2

Fractionation of Curdlan based on the difference of solubility in water:

Fifty grams of commercial Curdlan (sample No. 101) was suspended in distilled water, and fractionated by operations shown in the following flowsheet.

PREPARATION EXAMPLE 3

Preparation of a water-insoluble carbohydrate fraction of Curdlan by decomposition with formic acid:

45 g of sample No. 102 was decomposed with formic acid by the method of K. Ogawa et al. [Carbohydr. Res., 29, 397–403 (1973)). The operations are shown in the following flowsheet.

PREPARATION EXAMPLE 4-1

Re-fractionation by a molecular sieve of a water-soluble fraction of a formic acid decomposition product of Curdian:

0.15 g of the water-soluble fraction (sample No. 3) obtained in Preparation Example 3 was dissolved in ml of distilled water, and by GPC (column: TSK gel G3000 $PW_{XL} \times 2$, G2500 $PW_{XL} \times 1$; mobile phase: distilled water; flow rate: 0.5 ml/min.), 0.5 ml fractions were collected. By re-chromatography, six samples (Nos. 11 to 16) having different molecular weights were obtained.

PREPARATION EXAMPLE 4-2

Re-fractionation by a molecular sieve of a water-insoluble fraction of a formic acid degradation product of Curdlan:

0.2 g of the water-insoluble fraction (sample No. 4) obtained in Preparation Example 3 was dissolved in ml of 0.3M NaOH solution, and fractionated and rechromatographed in the same way as in Preparation Example 4-1 by GPC (column: TSK gel G3000 $PW_{XL} \times 2$, G2500 $PW_{XL} \times 1$; mobile phase: 0.3M NaOH solution; flow rate: 0.5 ml/min). A 0.3M HCl solution was added to the eluates for neutralization, and two samples (Nos. 17 and 18) having different molecular weights were obtained.

PREPARATION EXAMPLE 5

Preparation of a sample by sonication of a water-insoluble fraction of Curdlan:

One gram of sample No. 102 was suspended in about 100 ml of 5 mM NaOH, and under ice cooling, sonicated at 20 kHz and 80 kW for 12 minutes by Sonicator® (model 5202 PZT, made by Ohtake Works, Tokyo) to depolymerize it.

5M NaOH was added to the treated solution to prepare a 0.3M NaOH solution of the above sample, and fractionated by chromatography as in Preparation Example 4-2 to obtain eight samples (Nos. 19 to 22 and 103 to 106) having different molecular weights.

PREPARATION EXAMPLE 6-1

Preparation (I) of an inhibitor derived from a sea alga:

By the method of T. Usui et al., Agric. Biol. Chem. 43, 603–611 (1979), a commercial dry frond of *Eisenia bicyclis* (100 g; purchased from Suita Syoten, Co., Ltd., Tokyo) was ground to a powder and treated with 80% ethanol to remove a low-molecular-weight soluble fraction. A laminaran fraction was extracted from the residue by using a 2% aqueous solution of $CaCL_2$. 95% ethanol was added to the extract to prepare a solution of the laminaran fraction having a final ethanol concentration of 75%. The resulting precipitate was collected by centrifugal sedimentation and then washed with ethanol to obtain a crude laminaran sample. The crude sample was re-dissolved in distilled water and subjected to an anionic exchanger (DEAE-Toyopearl) to remove acidic substances (alginic acid, etc.) and pigments. The residual solution was again precipitated with ethanol to give sample No. 25.

PREPARATION EXAMPLE 6-2

Preparation (II) of an inhibitor derived from a sea alga:

In accordance with the method of J. J. Connell et al., J. Chem. Soc., 3494 (1950), 100 g of a commercial dry frond of *Laminaria japonica* (purchased from Suita Syoten Co., Ltd., Tokyo) was ground to a powder, and extracted with 0.09M HCl solution for 3 days. The insoluble matter was separated by filtration, and the filtrate was left to stand for 1 day. A small amount of precipitate that formed was removed by centrifugal separation, and 3 volumes of ethanol was added to the supernatant. The ppt was washed with an alcohol and dried to give a water-soluble laminaran fraction (sample No. 27).

PREPARATION EXAMPLE 7-1

Preparation (I) of an inhibitor derived from eumycetes:

Scretotan derived from *Sclerotinia libertiana* was obtained as follows:

By the method of Kitahara et al., Res. Bull. Fac. Agri. Gifu University 8, 100–105 (1957), a de-fatted dry powder (30 g) of the sclerotium of *Sclerotinia libertiana* was extracted fully with water. The residue was extracted with a 7% aqueous solution of NaOH. 10% $CuSO_4$ solution was added to the extract to form a precipitate. The precipitate was separated, washed with hydrochloric acid in methanol to remove copper, washed with 80% methanol to remove HCl and washed with methanol and ether, and dried. This procedure was repeated three times to purify the material, and 6 g of sample No. 28 was obtained.

PREPARATION EXAMPLE 7-2

Preparation (II) of an inhibitor derived from eumycetes:

A sample derived from *Schizophyllum commune* was obtained as follows:

By the method of Tabata et al., Carbohydr. Res., 89, 121–135 (1981), commercial schizophyllan (tradename Sonifilan produced by Kaken Chemical Co., Ltd.; medicine Lot No. J61040) was sonicated in aqueous solution for 10 hours in accordance with the procedure of Preparation Example 5. By fractionation with a molecular sieve under an alkaline condition, three samples (Nos. 29, 30 and 31) having different molecular weights were obtained.

PREPARATION EXAMPLE 7-3

Preparation (III) of an inhibitor derived from eumycetes:

A β-glucan sample derived from baker's yeast, *Saccharomyces cerevisiae* was obtained as follows:

Distilled water (50 ml) was added to 90 mg of commercial bakers' yeast glucan (Lot No. 56F-4027, a product of Sigma Chemical Co.), and the mixture was stirred at room temperature for 2 hours, and then centrifuged. About 50 ml of the supernatant was concentrated to 1 ml under reduced pressure. The insoluble matter was again removed by centrifugation, and 0.64 mg of sample No. 33 was obtained from the supernatant.

PREPARATION EXAMPLE 8

Preparation of a sample from barley β-glucan-:

Commercial barley β-glucan (a product of Sigma Chemical Co.; Lot No. 56F-0652) was dissolved in 0.3M NaOH to form its solution in a concentration of 5 mg/ml. By fractionation with a molecular sieve in an alkaline condition, a β-glucan sample (No. 36) having a narrow molecular weight distribution was prepared.

Separately, the above barley β-glucan was dissolved in hot water at a concentration of 5 mg/ml. The solution was centrifuged (3,500 rpm, 10 minutes). 100 µl of the supernatant was subjected 50 times to GPC using distilled water as a mobile phase in accordance with Preparation Example 4-1. The fractions were re-fractionated under the same conditions to give two samples (Nos. 37 and 38) having different molecular weights.

PREPARATION EXAMPLE 9

Preparation of partially carboxymethylated (1 →3)-β-D-glucan (average degree of substitution: 0.63):

A water-insoluble fraction of Curdlan obtained in accordance with Preparation Example 2 was carboxy-methylated by the method of A. E. Clarke and B. A. Stone [Phytochemistry 1, 175–188 (1962)]. 100 g of the water-insoluble fraction of Curdlan was dissolved at 0° C. in 1 liter of a 5M aqueous solution of sodium hydroxide in a gaseous nitrogen flow. With stirring, a solution of 236 g of monochloroacetic acid in 200 ml of water was added dropwise. After the addition, the solution was stirred at 60° to 65° C. for 2 hours. The resulting gel was strongly agitated in 2.5 volumes of ethanol to form fine fragments and filtered. The residue was washed fully with 70% ethanol, then further washed with ethanol and ether, and dried. The product was dissolved in 7 liters of water, and neutralized with 1M acetic acid. Activated charcoal (40 g) was added. The mixture was stirred at room temperature for 1 hour, and filtered. The filtrate was concentrated under reduced pressure to a volume of 1 liter. Ethanol in three times its volume was added to the concentrate to form a precipitate. The precipitate was washed with ethanol and ether, and dried under reduced pressure on concentrated sulfuric acid to give 113.85 g of a partially carboxymethylated (1→3)-β-D-glucan.

The resulting glucan was found to have a degree of etherification (the degree of substitution) of 0.63 by measurement in accordance with the uranyl nitrate method of D. F. Durso [Methods in Carbohydrate Chem., VIII 127–129 (1980)]. This means that out of 3 hydroxyl groups in one glucose residue forming the polysaccharide chain, 0.63 hydroxyl group were substituted.

A 25 mg aliquot of the resulting partially carboxymethylated (1→3)-β-D-glucan was dissolved in 5 ml of a 0.1M aqueous solution of ammonium acetate, and fractionated by GPC (column: Toyopearl HW65F, 5×100 cm; mobile phase: 0.1M aqueous solution of ammonium acetate; flow rate: 5.8 ml/min), and re-fractionated by GPC using other columns (columns: TSK gel G6000 $PW_{XL}$+G500 $PW_{XL}$ connected in series; mobile phase: 0.1M aqueous solution of ammonium acetate; flow rate: 0.6 ml/min.) to obtain sample No. 41 (Mn=231,000) having a narrow molecular weight distribution.

Furthermore, 0.3 g of the partially carboxymethylated (1→3)-β-D-glucan was dissolved in 30 ml of distilled water, and sonicated (9 KHz, 180–130 W, 1 hour) by a sonicator (insonator Model 201M, made by Kubota Works) to depolymerize it. A portion (4.5 ml) of the depolymerized product was mixed with 0.5 ml of a 1M aqueous solution of ammonium acetate. The mixture was. subjected to GPC fractionation and GPC re-fractionation by the same procedure as in the procedure of obtaining sample No. 41 to give two samples (Nos. 39 and 40) having different molecular weights.

PREPARATION EXAMPLE 10

Preparation of a partially carboxymethylated (1→3)-β-D-glucan having a degree of substitution of 1.2:

Ten grams of the carboxymethylated (1→3)-β-D-glucan having a degree of substitution of 0.63 obtained in Preparation Example 9 was added to 25 ml of 10.5M NaOH in a gaseous nitrogen flow and prepared into a paste. With vigorous stirring, 10 g (12 ml) of an aqueous solution of monochloroacetic acid was added. The mixture was warmed to 60° C. and stirred for 4 hours. After cooling, 30 ml of 2M HCl was added, and the solution was poured into 200 ml of hydrochloric acid in ethanol (40 ml HCl/ethanol). The resulting precipitate was collected, washed with 70% ethanol and further with ethanol and ether, and dried under reduced pressure to give sample No. 107.

The degree of substitution of this sample was 1.20, measured by the same method as in the case of Preparation Example 9.

PREPARATION EXAMPLE 11

Preparation of partially carboxymethylated laminaran:

Partially carboxymethylated laminaran was prepared by treating laminaran (Lot No. 77F-3885 of Sigma Chemical Co.) of *Laminaria digitata* by the method of A. E. Clarke and B. A. Stone: Phytochem. 1, 175 (1962) in the same way as in the method of partial carboxy-methylation in Preparation Example 9. Thus, sample No. 42 having a degree of substitution of 0.06 was obtained.

PREPARATION EXAMPLE 12

Preparation of partially methylated (1→3)-β-D-glucan:

In accordance with the method of M. Samec, Kolloid-Beihefte 51, 369 (1940), 3.0 g of a water-insoluble fraction of Curdlan obtained as in Preparation Example 2 was suspended in 80 ml of water, and in a gaseous nitrogen flow, 1.35 ml of a saturated aqueous solution of sodium hydroxide was added to dissolve the water-insoluble fraction completely. At 4° C., 60 g of dimethylsulfate was gradually added, and in about 1 hour, the reaction solution was added dropwise to acetone. The resulting precipitate was collected, thoroughly washed with acetone, and dried over conc. sulfuric acid under reduced pressure to give 3.13 g (sample No.43; degree of substitution: 0.16).

PREPARATION EXAMPLE 13

Preparation of partially sulfated laminaran:

Sulfation of laminaran from *Laminaria digitata* was carried out in pyridine by the following procedure using a pyridine-sulfur trioxide complex (Lot No. PPL 8823 of Wako Pure Chemical Industries).

0.5 g of thoroughly dried laminaran (Sigma Chemical Co.; Lot No. 77F-3885) of *Laminaria digitata* was dissolved in 50 ml of dehydrated pyridine, and 1 g of a pyridine-sulfur trioxide complex was added. The reaction was carried out at 60° C. for 1 hour. Water (100 ml) was added to the reaction mixture with cooling. It was then neutralized with sodium hydroxide and dialyzed against water through a dialysis membrane (spectropore; molecular weight 1.000 cut) which had been washed fully with an alkaline aqueous solution to remove the glucan. The dialyzate was concentrated and 2 times its volume of acetone was added to precipitate the carbohydrate component. The carbohydrate component was washed with acetone, and dried over conc. sulfuric acid under reduced pressure to give 0.38 g (sample No. 44 with a degree of substitution of 0.14).

The degrees of substitution of methyl groups and sulfate groups in the preparations obtained in Preparation Examples 12 to 13 were measured and calculated in accordance with the method described in (1) Ochiai, Tsuda and Sakamoto: "Yuki Teiryo Bunsekiho (Biryo)" [(Methods of Organic Quantitative Analysis (Tiny Amounts)], Nanzando (1956); and (2) Whistler, R. L. ed., Method in Carbohydrate Chemistry III, pages 229–235, 277–280 (1964), Academic Press.

COMMERCIAL SAMPLES

The properties of the following commercial samples were determined. The samples were directly subjected to measurements of the following alkali-solubilization and neutralization.

Glucose (JIS special graded reagent; Wako Pure Chemical Industries; sample No. 108)

Laminarioligosaccharides (pure reagent, Seikagaku Kogyo Co., Ltd.; samples Nos. 5 to 10)

Laminaran derived from *Eisenia araborea* (reagent of Nakarai Chemical Co., Ltd.; sample No. 23)

Laminaran derived from *E. araborea* (Tokyo Kasei Kogyo Co., Ltd.; sample No. 24)

Laminaran derived from *Laminaria digitata* (reagent of Sigma Chemical Co.; sample No. 26)

Lentinan derived from *Lentinus edodes* (a product of Yamanouchi Pharmaceutical Co., Ltd., medicine lot No. CKC7; sample No. 32)

Lichenan derived from *Cetraria islandica* (reagent of Sigma Chemical Co.; sample No. 34)

Lichenan derived from *Usnea barbata* (reagent of Sigma Chemical Co.; sample No. 35)

EXAMPLES 1–44

The molecular weights and factor G activation inhibiting titers of the above samples were measured, and the results are shown in Table 2.

TABLE 2

| Sample No. | Substance | Method of preparation | Carbohydrate structure (*1) | Mn (*2) | Mw/Mn | Factor G activation inhibiting titer (units/mg) |
|---|---|---|---|---|---|---|
| 1 | GPC fraction of Curdlan | PE (*3) 1 | (1) | 3,050 | 1.29 | 1,000,000 |
| 2 | Water-soluble fraction of Curdlan Formic acid regradation product of C*rdlan | PE 2 | (1) | 3,270 | 2.49 | 2,240,000 |
| 3 | Water-soluble fraction | PE 3 | (1) | 2,080 | 1.90 | 10,700,000 |

TABLE 2-continued

| Sample No. | Substance | Method of preparation | Carbohydrate structure (*1) | Mn (*2) | Mw/Mn | Factor G activation inhibiting titer (units/mg) |
|---|---|---|---|---|---|---|
| 4 | Water-insoluble fraction | PE 3 | (1) | 10,000 | 3.19 | 324,000 |
| 5 | Laminaribiose | Commercial (Seikagaku Kogyo) | (1) | 342 | | 214 |
| 6 | Laminaritriose | Commercial (Seikagaku Kogyo) | (1) | 504 | | 4,670 |
| 7 | Laminaritetraose | Commercial (Seikagaku Kogyo) | (1) | 667 | | 20,000 |
| 8 | Laminaripentaose | Commercial (Seikagaku Kogyo) | (1) | 829 | | 39,800 |
| 9 | Laminarihexaose | Commercial (Seikagaku Kogyo) | (1) | 991 | | 55,000 |
| 10 | Laminariheptaose | Commercial (Seikagaku Kogyo) | (1) | 1,153 | | 103,000 |
| | Formic acid degradation product of Curdlan | | | | | |
| 11 | GPC fraction 1 | PE 4-1 | (1) | 2,370 | 1.20 | 708,000 |
| 12 | GPC fraction 2 | PE 4-1 | (1) | 3,400 | 1.20 | 13,400,000 |
| 13 | GPC fraction 3 | PE 4-1 | (1) | 4,800 | 1.20 | 20,000,000 |
| 14 | GPC fraction 4 | PE 4-1 | (1) | 5,800 | 1.20 | 31,600,000 |
| 15 | GPC fraction 5 | PE 4-1 | (1) | 6,800 | 1.20 | 6,310,000 |
| 16 | GPC fraction 6 | PE 4-1 | (1) | 9,800 | 1.22 | 3,980,000 |
| 17 | GPC fraction 7 | PE 4-2 | (1) | 14,500 | 1.24 | 1,820,000 |
| 18 | GPC fraction 8 | PE 4-2 | (1) | 27,500 | 1.26 | 126,000 |
| | Sonicated product of Curdlan | | | | | |
| 19 | GPC fraction 1 | PE 5 | (1) | 20,700 | 1.27 | 646,000 |
| 20 | GPC fraction 2 | PE 5 | (1) | 28,300 | 1.18 | 389,000 |
| 21 | GPC fraction 3 | PE 5 | (1) | 50,200 | 1.26 | 4,900 |
| 22 | GPC fraction 4 | PE 5 | (1) | 58,100 | 1.29 | 234 |
| | Laminaran | | | | | |
| 23 | from Eisenia araborea | Commercial (Nakarai Chemical) | (2)a | 16,800 | 1.49 | 6,760 |
| 24 | from E. arborea | Commercial (Tokyo Kasei) | (2)a | 11,200 | 1.55 | 29,500 |
| 25 | from E. bicyclis | PE 6-1 | (2)a | 22,500 | 1.27 | 64,600 |
| 26 | from Laminaria digitata | Commercial (Sigma Chemical) | (2)b | 5,850 | 1.16 | 7,080,000 |
| 27 | from L. japonica | PE 6-2 | (2)b | 17,700 | 3.98 | 39,800 |
| 28 | Sclerotan | PE 7-1 | (2)d | 16,800 | 2.77 | 26,300 |
| | Schizophyllan | | | | | |
| 29 | GPC fraction 1 | PE 7-2 | (2)d | 6,750 | 3.14 | 138,000 |
| 30 | GPC fraction 2 | PE 7-2 | (2)d | 23,600 | 2.37 | 11,700 |
| 31 | GPC fraction 3 | PE 7-2 | (2)d | 27,500 | 1.49 | 50,100 |
| 32 | Lentinan | Commercial (Yamanouchi Pharm.) | (2)d | 21,200 | 2.63 | 10,000 |
| 33 | Water-soluble fraction of bakers' yeast glucan | PE 7-3 | (2)e | 11,600 | 5.14 | 11,500 |
| | Lichenan | | | | | |
| 34 | from Cetraria islandica | Commercial (Shigma Chemical) | (3) | 22,000 | 4.72 | 3,550 |
| 35 | from Usnea barbata | Commercial (Shigma Chemical) | (3) | 23,200 | 4.07 | 120 |
| | Barley β-glucan | | | | | |
| 36 | GPC fraction 1 | PE 8 | (3) | 54,900 | 1.16 | 30,900 |
| 37 | GPC fraction 2 | PE 8 | (3) | 129,000 | 1.09 | 11,700 |
| 38 | GPC fraction 3 | PE 8 | (3) | 200,000 | 1.13 | 40,700 |
| | Partially carboxymethylated $(1 \to 3)$-β-D-glucan (DS = 0.63) | | | | | |
| 39 | GPC fraction 1 | PE 9 | (1) | 42,400 | 1.14 | 117,000 |
| 40 | GPC fraction 2 | PE 9 | (1) | 77,300 | 1.10 | 91,200 |
| 41 | GPC fraction 3 | PE 9 | (1) | 231,000 | 1.10 | 80,000 |
| 42 | Partially carboxymethylated laminaran | PE 11 | (2)b | 8,170 | 1.21 | 3,630,000 |
| 43 | Partially methylated $(1 \to 3)$-β-D-glucan | PE 12 | (1) | 78,200 | 1.10 | 93,300 |
| 44 | Partially sulfated laminaran | PE 13 | (2)b | 10,300 | 2.04 | 117,000 |
| 101 | Curdlan | Commercial (Wako Pure Chemical) | (1) | 136,000< | 2.76< | 100> |
| 102 | Water-insoluble fraction of Curdlan | PE 2 | (1) | 159,000< | 2.50< | 100> |
| | Sonicated product of Curdlan | | | | | |
| 103 | GPC fraction 5 | PE 5 | (1) | 76,300 | 1.26 | 100> |
| 104 | GPC fraction 6 | PE 5 | (1) | 92,600 | 1.23 | 100> |

TABLE 2-continued

| Sample No. | Substance | Method of preparation | Carbohydrate structure (*1) | Mn (*2) | Mw/Mn | Factor G activation inhibiting titer (units/mg) |
|---|---|---|---|---|---|---|
| 105 | GPC fraction 7 | PE 5 | (1) | 171,000 | 1.19 | 100> |
| 106 | GPC fraction 8 | PE 5 | (1) | 216,000 | 1.19 | 100> |
| 107 | Partially carboxymethylated (1 → 3)-β-D-glucan (DS = 1.20) | PE 10 | (1) | 329,000< | 1.27< | 100> |
| 108 | Glucose | Commercial (Wako Pure Chemical) | | 180 | | 100> |

Notes to Table 2
(*1): The numbers are classification numbers given in the specification.
(*2): The molecular weights of glucose and laminarioligosaccharide are absolute molecular weights (theoretical values), and the molecular weights of the other samples are those calculated for polyethylene oxide and polyethylene glycol determined by the measuring method described below.
(*3): PE stands for Preparation Example.

Samples Nos. 1 to 44 are factor G activation inhibitors of this invention, while samples Nos. 101 to 108 are for comparison.

The molecular weights in the table are number average molecular weights (Mn) defined by the following equation and determined by GPC. The molecular weight distribution is expressed by a polydispersity (Mw/Mn)

$$\text{Number average molecular weight } (Mn) = \frac{\Sigma Hi}{\Sigma(Hi/Mi)}$$

$$\text{Weight average molecular weight } (Mw) = \frac{\Sigma(Hi \times Mi)}{\Sigma Hi}$$

$$\text{Polydispersity} = Mw/Mn$$

In the above equations, Hi represents the height of the ith peak (sample concentration) when the chromatogram is multidivided into equal parts by time, and Mi represents the molecular weight of the ith peak.

The factor G activation inhibiting titer was measured by the "method of measuring the titer of the activity of a factor G activation inhibitor" described below and expressed in units/mg.

Method of measuring the titer of the activity of a factor G activation inhibitor (sometimes abbreviated as GI):

Two hundred microliters of the reaction mixture contained the following materials.

(1) Assay sample (note 1) GI sample or distilled water 50 microliters
(factor G activating substance (abbeviated as GA, note 2) 10 pg or not added
(2) proclotting enzyme fraction of LAL $A_{280}$ = 2.5; note 3) 30 microliters
(3) factor G fraction of LAL ($A_{280}$ = 0.9; note 3) 20 microliters
(4) Tris-HCl buffer (pH 8.0) 20 μmoles
(5) $MgCl_2$ 20 μmoles
(6) Boc-Leu-Gly-Arg-pNA 0.13 μmole The above reaction mixture was incubated at 37° C. for 30 minutes, and 0.5 ml each of 0.04% sodium nitrite (0.48M HCl solution), 0.3% ammonium sulfamate, and 0.07% N-(1-naphthyl)ethylenediamine dihydrochloride were successively added, and its color was changed by diazo coupling. The amount of pNA liberated was measured as the absorbance at 545 nm ($A_{545}$).

The GI activity was calculated from the following equation.

$$GI \text{ activity } (\%) = 100 - \frac{[A_{545} \text{ of } GI \text{ sample containing } GA] - [A_{545} \text{ of pure water not containing } GA]}{[A_{545} \text{ of pure water containing } GA] - [A_{545} \text{ of pure water not containing } GA]} \times 100$$

The amount of GI which inhibited activation of factor G by GA under these conditions to an extent of is defined as 100 units.

(Note 1)
A sample which is water-insoluble is used after it is dissolved in 0.3M NaOH, and neutralized with an equal volume of 0.3M HCl.

(Note 2)
A GPC fractionated pure sample of the sonicated product of Curdlan which was prepared in Preparation Example 5 (Table 2, sample No. 106 having a molecular weight of 216,000).

(Note 3)
Prepared from horseshoe crab, T. tridentatus, inhabiting the coast of Japan in accordance with the method described in T. Obayashi et al., Clin. Chim. Acta, 149, 55–65 (1985).

The following conclusions may be drawn from the data given in Table 2.

(a) Commercial Curdlan (sample No. 101) known as a factor G activating substance contains a factor G activation inhibitor which is water-soluble and has a low molecular weight (samples Nos. 1 and 2).

(b) polyglycosides in which the number of connected (1→3)-β-D-glucoside structural units constituting the (1→3)-β-D-glucoside structure portion is 2 to 370 show a factor G activation inhibiting action.

(c) Fractions having a molecular weight of not more than 60,000 obtained by various depolymerization operations from the high molecular weight β-glucan fraction (sample No. 102) with no appreciable inhibitory activity exhibited factor G activation inhibiting titers (samples Nos. 3, 4 and 11 to 22).

(d) Fractions (Preparation Example 8, Samples Nos. 36, 37 and 38) obtained from barley glucan in which poly(1→3)-β-D-glucoside structure portions having a degree of not more than 10 and poly(1→4)-β-D-glucoside structural portions are linked to each other in blocks [see Ballance et al.,

Carbohyd. Res., 61, 107–118 (1978)] show activity equivalent to laminaritetraose or laminaripentaose, and can be used as the inhibitor of the invention whether the glucan as a whole has a molecular weight of more than 60,000 or less than 60,000.

(e) The partially carboxymethylated (1→3)-β-D-glucan having an average degree of substitution of at least 1.0 obtained in Preparation Example 10 (sample No. 107 (DS=1.2) lost its factor G activation inhibiting effect. When sample No. 26 having a high factor G activation inhibiting titer was partially carboxymethylated (Preparation Example 11) to reduce the chain length of the (1→3)-β-D-glucoside portion (sample No. 42), and when in Preparation Example 13, the (1→3)-β-D-glucoside structure portion was shortened by sulfate modification, the factor G activation inhibiting effects were reduced.

(f) When glucan having a degree of polymerization of at least 370 in the (1→3)-β-D-glucoside structure portion and a molecular weight of more than 60,000 was partially methylated (preparation Example 12) or partially carboxymethylated (Preparation Example 9, sample No. 41) to attain the structure defined in this invention, the resulting product had a factor G activation inhibitory effect.

Operating Mechanism of the Inhibitor of This Invention on Factor G

The factor G activation pathway in the horseshoe crab blood coagulating system is shown by the following chart, as reported in T. Morita et al., FEBS Letters, 129, 318–321 (1981).

The following experiment was conducted in order to determine what part of the above coagulation pathway the inhibitor of this invention inhibits.

A reaction mixture of the following composition was used. Two hundred microliters of the reaction mixture contained 5 micrograms of a factor G activation inhibitor (laminariheptaose; sample No. 10; abbreviated as I), 3 pg of a factor G activating substance (GPC fraction of sonicated Curdlan; sample No. 106; abbreviated as A), 20 microliters of a factor G fraction (abbreviated as G) and 30 microliters of a proclotting enzyme fraction (abbreviated as P) prepared from LAL by the method described in T. Obayashi et al., Clin. Chim. Acta, 149, 55–65 (1985), 20 µmoles of Tris-HCl buffer (pH 8.0), 20 µmoles of $MgCl_2$ and 0.13 µmole of a chromogenic substrate Boc—Leu—Gly—Arg—pNA (abbreviated as S).

In each of Runs 1 to 5, the sequence of adding the ingredients and the incubating conditions were varied, and the degree of inhibition of the factor G pathway was measured and determined in comparison with a control in which no inhibitor was added. The results are shown below.

| Experiment | Inhibition rate (%) to the control |
|---|---|
| 1  G+A+I+P+S  [0° C.]  $\xrightarrow{37° C., 10\,min.}$ | 100 |
| 2  G+A+I  [0° C.]  $\xrightarrow{37° C., 30\,min.}$  +P+S  $\xrightarrow{37° C., 3\,min.}$ | 100 |
| 3  G+I  [0° C.]  $\xrightarrow{37° C., 30\,min.}$  +A  $\xrightarrow{37° C., 10\,min.}$  +P+S  $\xrightarrow{37° C., 10\,min.}$ | 100 |
| 4  G+A  [0° C.]  $\xrightarrow{37° C., 30\,min.}$  +I  $\xrightarrow{37° C., 10\,min.}$  +P+S  $\xrightarrow{37° C., 10\,min.}$ | 1.7 |
| 5  G+A+P  [0° C.]  $\xrightarrow{37° C., 30\,min.}$  +I  $\xrightarrow{37° C., 10\,min.}$  +S  $\xrightarrow{37° C., 3\,min.}$ | 0 |

It is clear from Runs Nos. 1 to 3 that when the inhibitor (I) of this invention was added to factor G (precursor), the activation of factor G was inhibited to an extent of 100% irrespective of the presence of the factor G activating substance (A).

On the other hand, it is clearly seen from Runs Nos. 4 and 5 that once factor G was activated by (A), the activated factor G did not undergo inhibition even in the presence of the inhibitor (I).

It can be concluded therefore that the inhibitor (I) of this invention acts only on factor G (precursor).

In the presence of the inhibitor (I) of this invention in an amount sufficient to inhibit 100% of factor G in LAL, factor G does not undergo activation in whatever large amount of the activating substance (A) is present. It was confirmed however that if a large amount of the activating substance (A) is present in the presence of the inhibitor (I) in an amount smaller than that required to inhibit factor G to an extent of 100%, that portion of factor G which remains uninhibited by the inhibitor (I) is activated by the activating substance (A).

Accordingly, the existence of the maximum activating concentration of the (1→3)-β-D-glucan derivatives pointed out by A. Kakinuma et al., Biochem. Biophys. Res. Commun., 101, 434–439 (1981) or the various β-glucans shown by T. Morita et al., Prog. Chim. Biol. Res., 189, 53–64 (1985) in their ability to activate horseshoe crab factor G could be analyzed by the above experiment and analysis.

EXAMPLE 45

Comparison of the ability with specific assay of endotoxins between a kit containing a factor G activation inhibitor and a kit not containing it:

By using various assay samples, endotoxin specificities were compared by the following procedure when the factor G activation inhibitor of the invention was added to LAL-Test and when it was not added to LAL-Test.

The LAL-Test was a Toxicolor Test (colorimetry, Seikagaku Kogyo Co., Ltd.) having the following composition.

(1) Perchloric acid, (2) sodium hydroxide, (3) buffer, (4) lysate+chromogenic substrate, (5) endotoxin-free distilled water, (6) standard endotoxin, (7) hydrochloric acid, (8) sodium nitrite, (9) ammonium sulfamate, (10) N-(1-naphthyl)ethylenediamine dihydrochloride.

A group of reaction solutions (kit-A) were prepared by dissolving sample No. 13 as a factor G activation inhibitor in the buffer (3) at a concentration of 5 micrograms/ml, and dissolving the LAL reaction reagent in the solution. A group of reaction solutions (kit-B) were prepared by dissolving (4) in the buffer (3) not containing the inhibitor. The reactivities of the kits A and B with the assay samples were compared and are shown in Table 3.

TABLE 3

Comparison of endotoxin-specificities between the presence and absence of factor G activation inhibitor

| Sample No. | Amount per 0.1 ml of the sample | Reactivity ($\Delta A_{405}$/30 min.) Kit-A | Reactivity ($\Delta A_{405}$/30 min.) Kit-B |
|---|---|---|---|
| 1. Endotoxin (E.T.) (*1) | 2.5 pg | 0.447 | 0.448 |
|  | 5.0 pg | 0.895 | 0.894 |
| 2. Factor G activating substance (*2) | 3.0 pg | 0.000 | 0.232 |
|  | 100 ng | 0.001 | 1.5< |
| 3. Factor G activating substance + E.T. | 3.0 pg + 2.5 pg | 0.447 | 0.678 |
| 4. Washing from dialysis membrane (*3) | 8.0 pg | 0.001 | 0.312 |
| 5. Washing from dialysis membrane + E.T. | 8.0 pg + 2.5 pg | 0.446 | 0.757 |
| 6. Clinical samples as plasma a(*4) | 0.017 ml | 0.003 + 0.002 | 0.008 + 0.004 |
| b | " | 0.265 | 0.272 |
| c | " | 0.261 | 0.266 |
| d | " | 0.213 | 0.210 |
| e | " | 0.131 | 0.138 |
| f | " | 0.101 | 0.107 |
| g | " | 0.073 | 0.071 |
| h | " | 0.000 | 1.166 |
| i | " | 0.000 | 0.904 |
| j | " | 0.003 | 0.304 |

TABLE 3-continued

Comparison of endotoxin-specificities between the presence and absence of factor G activation inhibitor

| Sample No. | Amount per 0.1 ml of the sample | Reactivity ($\Delta A_{545}$/30 min.) Kit-A | Reactivity ($\Delta A_{545}$/30 min.) Kit-B |
|---|---|---|---|
| k | " | 0.001 | 0.203 |
| l | " | 0.004 | 0.152 |
| m | " | 0.007 | 1.5< |
| n | " | 0.006 | 1.5< |
| o | " | 0.006 | 1.5< |
| p | " | 0.003 | 1.5< |
| q | " | 0.005 | 1.5< |
| r | " | 0.004 | 1.5< |

Notes to TABLE 3:
(*1): *Escherichia coli* 0111:B4 derived endotoxin (Difco Laboratories Inc.)
(*2): Water-insoluble fraction of Curdlan; molecular weight >159,000; sample No. 102 in Table 2.
(*3): Washing resulting from perfusion distilled water through a hollow fiber-type hemodialyzer (AM-Neo-3000; a product of Asahi Medical Co., Ltd.) constructed by using a cuprammonium rayon membrane (regenerated cellulose membrane). Its carbohydrate content was determined by the phenol-sulfuric acid method.
(*4): Values for normal samples (n = 25) are means ± standard deviations.

Samples b to j were suspected of having a complication of sepsis. Blood cultures were positive for *Escherichia coli* in samples b to e; for *Pseudomonas aeruginosa* in samples f and g; for *Candida albicans* in sample i; and for *Candida guilliermondii* in sample j. Sample h was from a case of pulmonary aspergillosis, samples k and l from cases of systemic fungal infection determined at autopsy, and samples m to r from cases of chronic renal failure (without microbial infection) under hemodialysis with a hollow fiber-type hemodialyzer made by using cuprammonium rayon (regenerated cellulose).

Samples Nos. 1 to 5 were directly dissolved in a solvent, and 0.1 ml of each solution was used in the reaction, in accordance with the manual of the Toxicolor Test. Samples No. 6 (a to r) were obtained by pretreating plasma samples with the components (1) and (2) of the kit, and 0.1 ml of each of the pretreated products was used in the reaction, in accordance with the method of T. Obayashi [J. Lab. Clin. Med., 104, 321–330 (1984)].

Each of the samples was added to the reaction solutions prepared by using components (3) and (4), and reacted at 37° C. for 30 minutes. The resulting pNA was colored with coupling reagents (7) to (10). The reactivities of kits A and B were expressed by the absorbance at 545 nm.

The maximum reactivity of the present kit composition, $\Delta A_{545}$, was 1.5.

As can be seen from Table 3, kit-A containing the factor G activation inhibitor of the invention and kit-B as a conventional kit not containing the inhibitor showed the same reactivity with the endotoxin (sample No. 1). Kit-B showed a very high level of reactivity with the water-insoluble fraction of Curdlan (sample No. 2) as the factor G activating substance. On the other hand, kit-A showed no reactivity with the above sample, but when the endotoxin (sample No. 1) was used in combination (sample No. 3), kit-A showed the same reactivity as with endotoxin (sample No. 1).

When a washing obtained by washing a cellulose dialysis membrane, known as a Limulus test-reactive material (non-endotoxic), was used as a sample (Nos. 4 and 5) [F. C. Pearson et al., Artif. Organs, 8, 291–298 (1984)], both kit-A and kit-B showed the same behaviors and results as in the case of water-insoluble fraction of Curdlan and/or the absence of an endotoxin.

The foregoing results led to the finding that the combined use of LAL with the factor G activation inhibitor of this invention makes possible the specific determination of an endotoxin.

The following can be said with respect to clinical blood samples for which the conventional LAL-Test cannot clearly determine whether the patient suffered from a case of true endotoxemia. Both kits-A and -B showed high reactivity with samples No.6, b to g in which the presence of Gram-negative bacteria was determined by culturing. On the other hand, kit-A showed no reactivity, and kit-B showed high reactivity, with samples (No. 6, h to l) in which the presence of eumycetes known to have $(1\rightarrow3)$-$\beta$-D-glucan on its cellular wall was determined. Further, kit A showed no reactivity with samples (No. 6; m to r) of cases of chronic renal failure under hemodialysis which cannot be regarded as suffering from endotoxemia in view of the clinical symptoms. Abnormally high values obtained with kit-B is presumably because of $(1\rightarrow3)$-$\beta$-D-glucan derived from the dialysis membrane.

Assaying of clinical samples suspected of infections and sepsis in which the presence of an endotoxin is not clear, like the samples described above offers the advantage that a true Gram-negative bacterial infection (endotoxemia) can be determined accurately, and that it can also detect mycosis. Hence, it permits early diagnosis of invading microbes, and enables proper selection of medication and treatment and also an analysis of a therapeutic effect. The provision of a kit containing the inhibitor of this invention can be expected to contribute greatly to an advance in medicine, particularly diagnosis and therapy.

The following Referential Examples show the preparation of kits for specific detection of endotoxins by combining LAL with the factor G activation inhibitor of the invention.

REFERENTIAL EXAMPLE 1

Method of making an endotoxin-specific assay by adding a factor G activation inhibitor to a commercial or a conventional Limulus test reagent at the time of detecting the endotoxin:

1—1. The Limulus test reagent (lyophilized product) was dissolved in a customary manner in a designated dissolving liquid (distilled water or buffer), and the factor G activation inhibitor was added together with, or separately from, an assay sample (the sequence of addition is arbitrary).

For example, 0.1 ml of distilled water was added to "Pregel-S" (lyophilized product; Limulus test product by the gellation method; Seikagaku Kogyo Co., Ltd.), and 0.01 ml (120 micrograms/ml LAL) of an aqueous solution of the inhibitor (a GPC fraction 4 of the formic acid degradation product of Curdlan; No. 14 in Table 2) and 0.1 mi of the sample were added. The mixture was gently shaken, and heated at 37° C. for 60 minutes while it was left to stand. The mixture reacted only with the endotoxin to form a gel.

1-2. An inhibitor was dissolved in advance in a dissolving liquid for the Limulus test reagent, and dissolving the Limulus test reagent in the resulting solution. When "Coatest® Endotoxin" (chromogenic Limulus test product by Kabi Vitrum) was used, one vial of LAL (lyophilized product) was first dissolved in 1.4 ml of distilled water having dissolved therein 0.7 microgram of the inhibitor (laminaran; No. 26 in Table 2). A sample (0.1 ml) was added to 0.1 ml (500 ng/ml of LAL) of the resulting solution. The mixture was heated at 37 ° C. for 10 minutes. When 0.2 ml of a buffer containing a synthetic substrate (S-2423) was added and the solution was heated at 37° C. for 3 minutes, the mixture reacted only with the endotoxin and the solution became yellow. In determination, 200 microliters of a 50% acetic acid solution was added, and the absorbance of the solution at 405 nm was measured.

REFERENTIAL EXAMPLE 2

Method of making an endotoxin-specific Limulus test reagent by adding a factor G activation inhibitor to LAL in advance:

2-1. Method of adding the inhibitor to commercial LAL (the so-called Limulus gellation test reagent) in advance.

When turbidimetric kinetic assay was to be performed by using Limulus HS-Test Wako, a lyophilized product of Wako Pure Chemical Industries, Ltd., one vial of LAL (lyophilized product) was dissolved in 5 ml of distilled water having dissolved therein 0.5 microgram of the inhibitor (a GPC fraction 4 of the formic acid degradation product of Curdlan; No. 14 in Table 2). 0.1 ml (100 ng/ml of LAL) was put in a reaction test tube, and 0.1 ml of a sample was further added. The mixture was gently shaken. The mixture was set at a predetermined light measuring position of an analysis module (37° C.) of an instrument for turbidimetric kinetic assay (Toxinometer ET-201 supplied by Wako Pure Chemical Industrie, Ltd.), and a start switch was depressed. The mixture reacted only with the endotoxin, and the gellation time was displayed.

2-2. Method of achieving the object by adding the inhibitor to LAL before addition of an assay sample.

For example, when turbidimetry was to be performed by using LAL, 0.01 ml (50 ng/ml of LAL) of a 1M Tris-HCl-1M MgCl$_2$ buffer (pH 8.0) having dissolved therein 0.5 microgram of the inhibitor (laminaran; No. 26 in Table 2) per ml was added to 0.1 ml of a lysate extracted from the amebocytes of *Tachypleus tridentatus* by using a hypotonic buffer solution. Then, 0.1 ml of an assay sample was added to the solution, and the mixture was heated at 37°C. The mixture reacted only with the endotoxin, and the solution became whitely turbid. The amount of the endotoxin could be determined by measuring the absorbance of the solution periodically at 660 nm.

REFERENTIAL EXAMPLE 3

Method of producing a lysate as a material for an endotoxin-specific Limulus test reagent by adding the factor G activation inhibitor at the time of extracting and preparing LAL:

Hemolymph was drawn from horseshoe crab (any of *Tachypleus tridentatus, T. gigas, Limulus polyphemus,* and *Carcinoscorpius rotundicauda*, and centrifuged to obtain amebocytes (about 20 g). Then 100 ml of an inhibitor solution obtained by dissolving 2.0 mg/liter of the inhibitor (partially carboxymethylated laminaran; No. 42 in Table 2) in distilled water or a hypotonic buffer solution such as 0.02M Tris-HCl buffer (pH 8.0) was added to the amebocytes. The mixture was homogenized by a Waring blender, and then centrifuged (8,000 rpm; 30 minutes; 4° C.) to separate it into a supernatant and a precipitate. This operation was repeated to give about 150 ml of the supernatants as LAL. A fixed amount of the resulting LAL was used in place of LAL extracted by a conventional method, and Limulus test reagents (gellation method, turbidimetric method, turbidimetric kinetic method, chromogenic synthetic substrate method) were prepared. The resulting reagent was an endotoxin-specific Limulus test reagent which specifically react only with endotoxins.

For production of an endotoxin-specific Limulus test reagent by the chromogenic substrate method, the use of the substrates disclosed, for example, in U.S. Pat. No. 4,495,294 (entitled: Method for Determining Bacterial Endotoxin and Kit Therefor) and such substrates as R—Ile—Glu—Ala—Arg—pNA and methoxycarbonyl-D-hexahydro-tyrosyl-Gly-Arg-pNA.AcOH (in which R represents an acetyl group, an α-N-benzoyl group, an α-N-carbobenzoxy group, an N-tert-butoxycarbonyl group, a p-toluenesulfonyl group or other amino acid N-terminal protecting groups will permit production of a reagent of high sensitivity.

For example, such a reagent can be produced by adding 1.5 micrograms of MgCl$_2$ and 4.0 micrograms of a synthetic substrate (N-tert-butoxycarbonyl-Leu-Gly-Arg-p-nitroanilide) to 0.04 ml of the lysate and lyophilizing the mixture. When 0.1 ml of 0.2M Tris-HCl buffer (pH 8.0) and 0.1 ml of an assay sample were added to the lyophilized product and the mixture was heated at 37° C. for 30 minutes, the mixture reacted only with endotoxin, and the solution assumed yellow.

An LAL reagent for the gellation method, the turbidimetric method and turbimetric kinetic assay could be produced by adding 10.0 micrograms of MgCl$_2$ to 0.1 ml of the lysate and lyophilizing the mixture. When this reagent was used as in Referential Examples 1-1, 2-1 and 2-2, it reacted only with an endotoxin.

Industrial Utilizability

The factor G activation inhibitor of this invention provides an endotoxin-specific LAL-Test reagent by combining it with LAL and is useful in assaying clinical samples suspected of infections and sepsis in which the presence or absence of an endotoxin is uncertain. It has an advantage of being able to determine accurately a true Gram-negative bacterial infection (endotoxemia), and by using a conventional LAL-Test in combination, mycosis can be detected. It permits early diagnosis of invading microbes, and enables proper selection of medication and treatment and also an analysis of a therapeutic effect. The provision of a kit containing the inhibitor of this invention can be expected to contribute greatly to an advance in medicine, particularly in diagnosis and therapy.

What is claimed is:

1. A method for assaying endotoxin in a sample specifically using horseshoe crab amebocyte lysate, wherein a polyglycoside composed of a poly-(1→3)-β-D-glucoside structural portion consisting of 2 to 370 (1→3)-β-D-glucoside structural units of the following formula:

which are continuously bound to one another is added in an amount sufficient to inhibit 100% of activation of factor G existing in said horseshoe crab amebocyte lysate.

2. The method for assaying endotoxin according to claim 1, wherein the polyglycoside is added either (1) at the time of assay, (2) to horseshoe crab amebocyte lysate beforehand, or (3) at the time of extracting and preparing horseshoe crab amebocyte lysate.

3. The method for assaying endotoxin according to claim 1, wherein the polyglycoside is obtained by a partial decomposition and/or a separation treatment of a carbohydrate chain.

4. The method for assaying endotoxin according to claim 1, wherein the polyglycoside is produced by depolymerizing a carbohydrate chain by a partial decomposition method selected from the group consisting of a hydrolysis with an acid, an alkali or β-glucanase, an acetolysis and a sonication, and/or fractionating a carbohydrate chain by a fractional precipitation method with an organic solvent or a salt, or a fractionation method with a molecular sieve agent or a molecular sieve membrane.

5. The method for assaying endotoxin according to claim 1 wherein the polyglycoside has a molecular weight of about 2,080 to about 5,800.

6. The method for assaying endotoxin according to claim 1 wherein the polyglycoside has a factor G activation inhibiting titer of at least 10,700,000 units/mg.

7. The method for assaying endotoxin according to claim 1, wherein the polyglycoside has a molecular weight of about 2,080 to about 5,800 and has a factor G activation inhibiting titer of at least 10,700,000 units/mg.

8. The method for assaying endotoxin according to claim i, wherein the polyglycoside has a molecular weight of about 2,080 and a factor G activation inhibiting titer of about 10,700,000 units/mg.

9. The method for assaying endotoxin according to claim 1, wherein the polyglycoside has a molecular eight of about 3,4000 and a factor G activation inhibiting titer of about 13,400,000 units/mg.

10. The method for assaying endotoxin according to claim 1, wherein the polyglycoside has a molecular weight of about 4,800 and a factor G activation inhibiting titer of about 20,000,000 units/mg.

11. The method for assaying endotoxin according to claim 1, wherein the polyglycoside has a molecular weight of about 5,800 and a factor G activation inhibiting titer of about 31,600,000 units/mg.

12. The method for assaying endotoxin according to claim 1, wherein the factor G activation inhibiting titer is measured by adding a factor G activating substance, a proclotting enzyme fraction of horseshoe crab amebocyte lysate, a factor G fraction of horseshoe crab amebocyte lysate, a buffer, magnesium chloride and a chromogenic substrate to a factor G activation inhibitor sample and quantifying an amount of a chromogenic group liberated after a definite time of incubation.

13. The method for assaying endotoxin according to claim 1, wherein the polyglycoside is added in an amount of 50 ng to 500 ng per ml of the horseshoe crab amebocyte lysate.

* * * * *